United States Patent [19]

Schwarz et al.

[11] Patent Number: 5,958,471

[45] Date of Patent: Sep. 28, 1999

[54] SPRAY DRIED POLYOL COMPOSITION AND METHOD OF MAKING

[75] Inventors: Eugen Schwarz, Bensheim; Gernot Möschl, Weiterstadt; Heinrich Nikolaus, Darmstadt; Ralf Steinsträsser, Rossdorf, all of Germany

[73] Assignee: Merck Patent Gesellschaft mit beschrankter Haftung, Germany

[21] Appl. No.: 08/669,470

[22] PCT Filed: Oct. 16, 1995

[86] PCT No.: PCT/EP95/04059

§ 371 Date: Jun. 8, 1996

§ 102(e) Date: Jun. 8, 1996

[87] PCT Pub. No.: WO96/14282

PCT Pub. Date: May 17, 1996

[30] Foreign Application Priority Data

Nov. 8, 1994 [DE] Germany ............................. 44 39 858

[51] Int. Cl.⁶ ................................ A23G 3/00; A23G 3/30; A23L 1/302

[52] U.S. Cl. .................................... 426/3; 426/72; 426/96; 426/471; 426/658

[58] Field of Search ..................................... 426/3, 658, 5, 426/6, 72, 96, 471, 285, 453

[56] References Cited

U.S. PATENT DOCUMENTS

| | | | |
|---|---|---|---|
| 4,971,806 | 11/1990 | Cherukuri et al. | 426/5 |
| 5,041,294 | 8/1991 | Patel | 426/3 |
| 5,043,169 | 8/1991 | Cherukuri et al. | 426/5 |
| 5,075,118 | 12/1991 | Di Falco et al. | 426/3 |
| 5,616,361 | 4/1997 | Virtanen et al. | 426/658 |

FOREIGN PATENT DOCUMENTS 277176  3/1990  Germany .

*Primary Examiner*—Arthur L. Corbin
*Attorney, Agent, or Firm*—Millen, White, Zelano & Branigan

[57] ABSTRACT

The invention relates to a spray dried composition consisting essentially of sorbitol, xylitol and mannitol, the method of making the composition and the use thereof in a compacted article or chewing gum products.

11 Claims, 1 Drawing Sheet

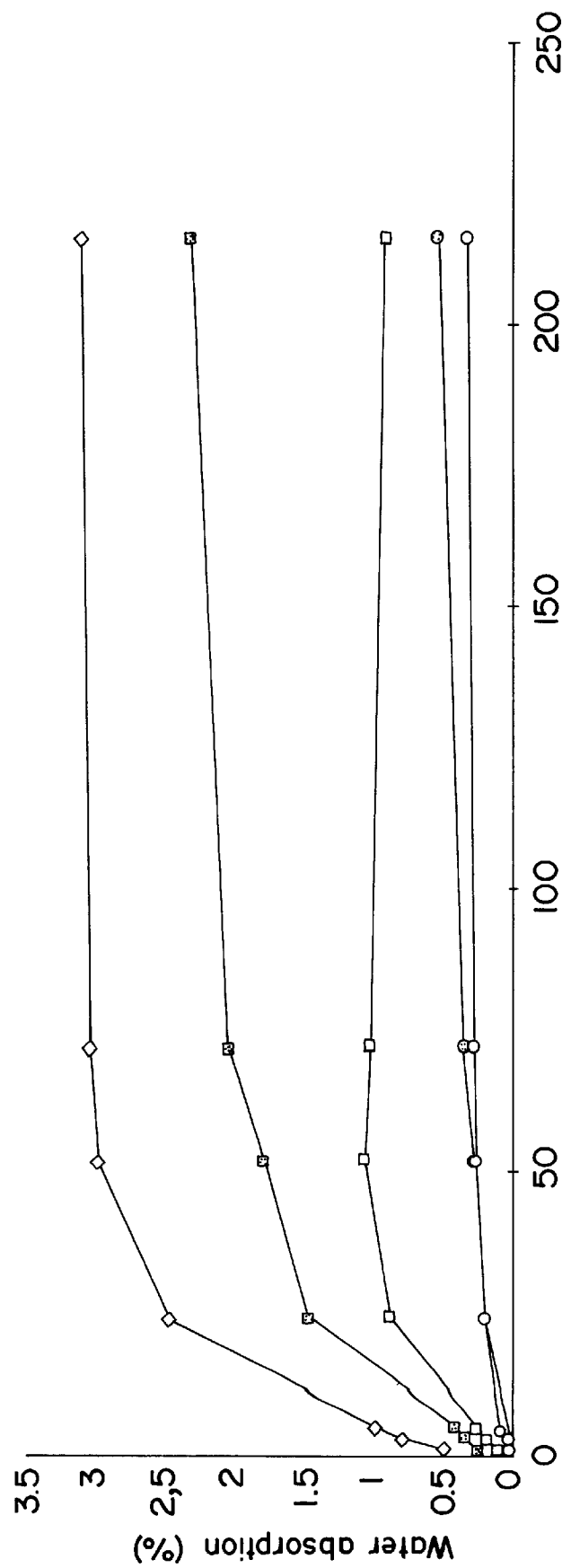

SPRAY DRIED POLYOL COMPOSITION AND METHOD OF MAKING

BACKGROUND OF THE INVENTION

The invention relates to a polyol composition obtainable by co-spray-drying.

Polyols and polyol mixtures are used to a great extent as additives and carriers, inter alia, for tablets for chewing and sucking, chewing gum and other products of the confectionery industry. The particular advantage of polyols is that they are suitable in principle even for direct compaction without further processing aids and additives. Polyols are generally produced by hydrogenation of their underlying carbohydrates. In solid form, they can be obtained both by crystallization and by spray-drying.

In the production of compacted articles, such polyols generally give a rough, not very satisfactory surface, or, in the case of polyol mixtures, in addition, a low hardness. Therefore, special processes have been developed in order to prepare polyols suitable for improved compaction.

In DE 32 45 170, it is proposed to prepare a polyol combination from sorbitol and 10 to 15% by weight of mannitol by spray-drying. This is intended to increase the flexural strength of tablets. There is no indication there that improved properties, in particular higher plasticity, can be achieved with polyol combinations containing other polyols or relatively low proportions of mannitol and obtainable by spray-drying.

Furthermore, a polyol of this type is less suitable for the production of chewing gum, since these become too hard after a short chewing time.

EP 0 528 604 describes a sorbitol and xylitol composition obtainable by co-melting. However, this leads to tablets having a comparatively low hardness.

SUMMARY OF THE INVENTION

The object was therefore to provide a polyol composition which can be produced without problems and whose tableting properties and plasticity are improved in comparison to known polyols.

It has now been found that a polyol composition obtainable by co-spray-drying comprising less than 10% by weight of mannitol gives a much smoother surface in tableting at the same pressing force and that this product may be processed to give chewing gums which have improved processing properties and remain soft much longer than chewing gum produced with conventional sorbitol or mixtures of sorbitol and other polyols.

The invention therefore relates to a composition essentially obtainable from at least two polyols by co-spray-drying which comprises less than 10% by weight of mannitol.

The term polyol means sugar alcohols of the general formula

$$HOCH_2-(CHOH)_n-CH_2OH$$

in which n is 2 to 6, preferably 3 to 4, and dimeric anhydrides thereof, in particular $C_{12}H_{24}O_{11}$.

In particular, the term polyols means hexitols such as sorbitol and mannitol, and pentitols such as xylitol, are possible as well as $C_4$-polyhydric alcohols such as erythritol or $C_{12}$-polyhydric alcohols such as lactitol. The term polyol composition means a composition of a plurality of polyols which differ markedly in their composition from compositions arising in the industrial preparation of sorbitol, preferably those compositions which comprise at least two polyols having a different number of C atoms, in particular the term means a composition comprising at least one hexitol and at least one pentitol.

Preferred embodiments are
  a) compositions obtainable by dissolving at least two polyols in water and spraying the resulting aqueous mixture in an air stream having a temperature of 120° to 300° C.
  b) compositions where sorbitol and xylitol or sorbitol, xylitol and mannitol are used as polyols.
  c) compositions where the ratio of sorbitol to xylitol is in a range between 50:50 and 99:1, in particular between 65:35 and 98:2.
  d) compositions where the ratio sorbitol:xylitol:mannitol is in a range between 90:1:9 or 70:29:1 and 98:1:1, in particular between 90:2:8 or 80:18:2 and 94:1:5 or 94:5:1.
  e) compositions where the content of water is lower than 1% by weight.
  f) compositions which absorbs more than 2% water within 24 hours during storage in a hygrostat at 55% relative humidity.

The invention further relates to compacted articles such as tablets for sucking or chewing and chewing gums, and confectionery comprising a composition of the invention.

The invention further relates to a process for the preparation of a composition essentially consisting of at least two polyols, including the following steps:
  a) preparing an aqueous solution of at least two polyols, where this solution has a mannitol content of less than 10% by weight, based on the total polyol content,
  b) spraying the resulting solution in an ascending air stream at a temperature between 120° and 300° C., where the water is evaporated, and
  c) isolating of the composition.

In a particularly preferred embodiment, the polyol composition of the invention essentially consists of 85 to 95% by weight, in particular 88 to 94% by weight, of sorbitol and 5 to 15% by weight, in particular 6 to 12% by weight, of one or two polyols selected from xylitol and mannitol.

Preferably, the polyol composition of the invention comprises less than 10% by weight, in particular less than 5% by weight, of mannitol.

An aqueous solution of at least two polyols is used for the spray-drying. The solids content is set in advance to about 30 to about 75% by weight, in particular 60 to 72% by weight, preferably by mixing two or more polyol solutions in the desired ratio. The spraying is carried out by atomizing by means of nozzles, preferably by means of a centrifugal atomizer into a dry centrifugally injected air stream heated to a temperature of 120°–300° C., preferably 140°–170° C. The amount of the polyol solution fed and of the injected hot air is matched so that the polyol is dried to a water content of about 0.3 to about 1% by weight. In any case, the water content should be below 1% by weight.

The polyol particles which are obtained in this process by dehydration of the polyol solution droplets are heated in the spray-drying to a temperature of about 50° to about 70° C., while the injected air cools to about the same temperature. The polyol composition is collected in vessels and, after cooling, is directly suitable for the production of compacted articles or chewing gum.

The polyol composition of the invention has a homogeneous appearance. The bulk density (as specified in DIN 53

912) is about 0.3 to 0.6 g/ml, and the tamped density (as specified in DIN 53 194) is about 0.4 to 0.7 g/ml. The particle size can be controlled in broad limits by the spray-drying process.

The polyol composition thus characterized has a number of advantageous tableting properties:

Surprisingly, it is possible to establish that, with the polyol composition of the invention, at the same pressing force, harder tablets having a markedly smoother surface can be produced than with the known compactible sorbitol types or polyol combinations obtainable by mechanical trituration or co-crystallization. Since the optimal strength of tablets for sucking is predetermined by the sucking behavior, this means that optimally smooth, hard tablets can be produced even at very low pressing forces. Tableting machines by which the polyol composition of the invention can be compacted can therefore operate at relatively low pressing forces and are subject to lower wear in this manner.

Owing to the irregular surface, the polyol composition of the invention is able to bind even relatively large amounts of additives, such as cocoa powder, colorants or other additives. Even in the case of a high loading with additives, homogeneous mixtures are obtained and the compacted articles produced therefrom have a uniform appearance.

Owing to the particular manner of preparation by spraying an aqueous solution, it is possible to distribute water-soluble additives, such as citric acid, sweeteners, in particular acesultame-K, aspartame, saccharin, cyclamate and sucralose, colorants, vitamins, in particular ascorbic acid and the like, completely homogeneously in the polyol composition or the compacted articles produced therefrom.

In addition to the polyol composition of the invention, the compacted articles of the invention comprise one or more constituents selected from:

pharmaceutically active compounds and substances permitted under food law. Preferred substances permitted under food law are natural, nature-identical or artificial aroma substances or flavorings, vitamins, trace elements, minerals, colorants,.. lubricants, release agents, sweeteners, stabilizers or antioxidants. The proportion of this constituent is preferably between 0.1 and 80%, in particular between 0.1 and 30%.

Particular preference is given to vitamin tablets containing one or more vitamins.

These compacted articles are produced in a manner known per se by mixing the constituents in dry form and then tableting them.

The polyol compositions of the invention have a significantly higher hygroscopicity than conventional polyols. Owing to this property, they are suitable, in particular, for the production of chewing gum.

The chewing gums of the invention comprise, in addition to the polyol combination, a gum base permitted under food law, one or more liquid polyhydric alcohols, in particular liquid sorbitol or glycerol and, if appropriate, one or more natural, nature-identical or artificial aroma substances.

These chewing gums generally consist of:
15–35% by weight of gum base
40–75% by weight of spray-dried polyol composition
15–25% by weight of one or more liquid polyhydric alcohols
0–5% by weight preferably 0.5 to 2% by weight, of one or more aroma substances The polyol composition of the invention can be used alone or with additives for all conventional purposes, in particular for the production of tablets for chewing and sucking and of chewing gum. Owing to the improved tableting properties, a considerable advance in this area is achieved by the invention.

Preparation examples:

Example 1:

A 70% strength aqueous solution which comprises 92.5 parts of sorbitol and 7.5 parts of xylitol, based on the dry matter, is prepared.

This polyol solution is sprayed at about 40° C. by means of a centrifugal atomizer into the upper part of a cylindrical stainless steel tower. At the same time, air heated to 160° C. and crystallized polyol are injected tangentially into the spray zone. As a result, the individual polyol droplets dry out and crystallize. The solids stream is conducted off via a cooling drum and then divided: part is recycled to the spray zone of the tower and the rest is screened, further dried via a fluidized bed and then packaged. The product thus obtained can be compacted without problems and leads to tablets having a very smooth surface, and to chewing gum having the advantages mentioned.

Example 2:

A 70% strength aqueous solution which comprises 92 parts of sorbitol, 5 parts of xylitol and 3 parts of mannitol, based on the dry matter, is prepared. The product obtained by spray-drying, analogously to Example 1, may be compacted without problems, results analogous to those given in Example 1 being achieved.

In the following application examples, a polyol composition prepared as in Example 1 or Example 2 is used.

| Example 3: Menthol tablets | |
|---|---|
| Polyol composition | 247.0 parts by weight |
| Menthol | 1.8 parts by weight |
| Magnesium stearate | 1.2 parts by weight |

The constituents are mixed and compacted at a pressing force of 14 KN to give tablets of 9 mm in diameter and a weight of 250 mg.

| Example 4: Tablets for caries prophylaxis | |
|---|---|
| Cetylamine hydrofluoride | 41.82 parts by weight |
| N-cetylpyridinium chloride | 18.00 parts by weight |
| Peppermint aroma | 40.00 parts by weight |
| Polyol composition | 1335.18 parts by weight |
| Sodium hydrogencarbonate | 825.00 parts by weight |
| Citric acid | 500.00 parts by weight |
| Fumaric acid | 240.00 parts by weight |

The constituents are mixed and compacted at a pressing force of 25 KN to give tablets of 20 mm in diameter and 3000 mg in weight.

| Example 5: Tablets for sucking | |
|---|---|
| Polyol composition prepared as in Example 2 with addition of 0.8% by weight of citric acid, based on sorbitol used | 491.0 parts by weight |
| Dried fruit aroma (various flavors) | 1.5 parts by weight |
| Magnesium stearate | 2.5 parts by weight |

The constituents are mixed and compacted at a pressing force of 30 KN to give tablets of 13 mm in diameter and 500 mg in weight.

| Example 6: Vitamin C tablets | |
| --- | --- |
| Ascorbic acid | 105.0 parts by weight |
| Orange aroma | 10.0 parts by weight |
| Polyol composition prepared as in Example 2 | 1377.5 parts by weight |
| Magnesium stearate | 7.5 parts by weight |

The constituents are mixed and compacted at a pressing force of 11 KN to give tablets of 18 mm in diameter and 1500 mg in weight.

| Example 7: Coffee tablets | |
| --- | --- |
| Polyol composition | 462.5 parts by weight |
| Coffee extract powder | 25.0 parts by weight |
| Caffeine | 10.0 parts by weight |
| Magnesium stearate | 2.5 parts by weight |

The constituents are mixed and compacted at a pressing force of 30 KN to give tablets of 13 mm in diameter and 500 mg in weight.

| Example 8: Multivitamin tablets | |
| --- | --- |
| Vitamin mixture: | |
| Thiamine nitrate | |
| Riboflavin | |
| Nicotinamide | |
| Pyridoxol hydrochloride | |
| Vitamin $B_{12}$ (0.1%) | |
| Vitamin A (325,000 I.U./g) | |
| Vitamin $D_3$ (100,000 I.U./g) | |
| Vitamin C (coated) | |
| Sodium ascorbate | |
| Vitamin E acetate (50%) | |
| Tableting mixture: | |
| Vitamin mixture | 147.0 parts by weight |
| Polyol composition obtainable in accordance with Example 2 with addition of 0.3% by weight of aspartame, based on sorbitol used | 563.29 parts by weight |
| Strawberry aroma | 2.00 parts by weight |
| Colorant | 0.20 parts by weight |
| Magnesium stearate | 22.11 parts by weight |

The constituents are mixed and compacted at a pressing force of 11 KN to give tablets of 737 mg in weight.

Example 9: Analysis of the tableting properties

Tablets were produced containing various polyols:

| Tablet diameter: | 11 mm | | Tablet weight: 450 mg | |
| --- | --- | --- | --- | --- |
| Tablet height: | 3.7 to 3.9 mm | | Pressing force: 12.5 KN | |
| Polyol | | | 99.5 parts by weight | |
| Magnesium stearate | | | 0.5 parts by weight | |
| Co-sprayed polyol from Example 2 | Mechanical polyol mixture (having a composition as in Example 2, but made from spray-dried sorbitol) | Mechanical polyol mixture (having a composition as in Example 2 from crystallized sorbitol) | Pure sorbitol, spray-dried | Pure sorbitol, crystallized |

Example 9: Analysis of the tableting properties

Tablet hardness:

| 442 N | 231 N | 218 N | 280 N | 235 N |
| --- | --- | --- | --- | --- |

Sucking behavior of the tablets:

| very smooth, supple | markedly rougher | markedly rougher | markedly rougher | highly markedly rougher |
| --- | --- | --- | --- | --- |

Necessary pressing force to achieve a tablet hardness of about 150 N (the necessary pressing force becomes an evaluation criterion):

Necessary pressing force:

| 5100 N | 7400 N | 10200 N | 6800 N | 8400 N |
| --- | --- | --- | --- | --- |

Sucking behavior of the tablets:

| smooth | noticeably rougher | noticeably rougher | noticeably rougher | markedly rougher |
| --- | --- | --- | --- | --- |

| Example 10: Spearmint chewing gum | |
| --- | --- |
| Framework formula: | |
| Gum base | 26.0% |
| Polyol composition | 52.5% |
| Sorbitol F, liquid | 16.0% |
| Glycerol | 4.0% |
| Spearmint aroma | 1.5% |

Example 11: Polyol composition from Example 2

Comparison Example A: Pure sorbitol instead of the polyol composition

Comparison Example B: Mechanical trituration consisting of 92% of sorbitol, 5% of xylitol and 3% of mannitol instead of the polyol composition These chewing gums are subjected to a sensory test and a penetrometer measurement:

A. Sensory test of the chewing gum bases according to the specified formula by the triangle test:

1st test: Two samples with the chewing gum according to Example 10. One sample with Comparison Example A 2nd test: One sample according to Example 10. Two samples with Comparison Example B.

Result: All the testers correctly established the differences in the chewing tests and correctly assigned all the samples.

The differences therefore recognized with 100% success rate indicate a high significance of the quality of the novel products.

The chewing gum using the polyol combinations of Example 10 from the co-spraying were highly rated, particularly with respect to the initial chewing behavior. Furthermore, they were notable owing to non-crumbling and non-sticky behavior. Solidification on exhaustive chewing proceeded more slowly than in the comparisons.

For this test, samples were used which had been stored for three weeks at room temperature.

B. Penetrometer measurements and general evaluations of the chewing gums

Description of the method:

The texture of plastic substances is measured with the penetrometer. Depending on the firmness of the product to be tested, a conically pointed cylinder or a needle-like pin is mounted in the instrument and is loaded with a defined weight.

After the measuring process has been started, the penetrating body acts owing to the force of gravity for a set precisely constant time period on the test product.

In the case of chewing gum bases, a special needle is used which, depending on the hardness and viscosity of the chewing gum bases, penetrates to a greater or lesser depth into the base heated to 40° C.

An initial plasticity is desirable which permits problem-free deformation of the chewing gums with low tackiness. Furthermore, a not excessive post-hardening of the finished products, which would lead to crumbling and poor initial chewing behavior of the bases, is desirable.

In addition, it is desirable even in the production that the additives such as sugar substitutes can readily be mixed in. Typical symptoms of defects in incorporation are clearly audible noises on air being drawn into and escaping from the base, the so-called "snapping" or "popping" during the mixing process.

In all of the formulas given, the polyol combination sweetened with saccharin or aspartame can also be used, or else a pigmented polyol combination can be used.

C. Study of the hygroscopicity (water absorption during storage in the hygrostat)

A sample of the composition of the invention is kept in a hygrostat, or various samples of differently prepared pure sorbitol or sorbitol preparations were kept in a hygrostat for a relatively long time at a relative humidity of 55%.

The water absorption of the individual samples can be taken from the table below:

TABLE

| Sample Time [h] | Example 2 Symbol ◆ | Example B (instant sorbitol) ■ | Example B (crystalline sorbitol) ● | Pure sorbitol (instant) □ | Pure sorbitol (crystalline) ○ |
|---|---|---|---|---|---|
| 1 | 0.49 | 0.18 | 0.02 | 0.1 | 0.02 |
| 5 | 1 | 0.41 | 0.03 | 0.25 | 0.09 |
| 24 | 2.48 | 1.48 | 0.19 | 0.89 | 0.19 |
| 72 | 3.01 | 2.03 | 0.35 | 1.03 | 0.27 |
| 216 | 3.6 | 2.30 | 0.53 | 0.91 | 0.32 |

| | Depth of penetrometer penetration (mm) | | | Incorporation | Appearance | Sensory properties |
|---|---|---|---|---|---|---|
| | 1 day | 7 days | 21 days | | | |
| Example 10 | 72 | 62 | 40 | no snapping, no popping | smooth, flexible | not sticky on initial chewing; little post-hardening on exhaustive chewing |
| Comparison Example B | 81 | 54 | 33 | some snapping and popping | almost smooth; not very flexible | somewhat sticky on initial chewing; rapid post-hardening on exhaustive chewing |
| Comparison Example A | 82 | 48 | 24 | marked snapping and popping | somewhat rough surface; not flexible | rough and sticky on initial chewing; rapid post-hardening on exhaustive chewing |

The grain size of the sorbitol types used was set in 10 each case to the usual spectrum for use in chewing gum bases.

The differences must be rated as significant in each case, that is also in the case of the penetrometer measurements.

BRIEF DESCRIPTION OF DRAWINGS

FIG. 1 shows the time course of water absorption of the individual samples during storage in the hygrostat.

The symbols used for the individual samples may be taken from the table given above.

The composition of the invention absorbs substantially more water than the other samples, by which means it remains supple for a long period.

We claim:

1. A composition comprising a product obtained by co-spray-drying, in an air stream at a temperature of 120° to 300° C., a mixture consisting essentially of sorbitol, xylitol and mannitol dissolved in water, and having a sorbitol content of 70–98% by weight, a xylitol content of 1–29% by weight and a mannitol content of 1–9% by weight.

2. The composition of claim 1, wherein the water content of the product is from about 0.3% to about 1% by weight.

3. The composition of claim 1, wherein the co-spray-drying is conducted in an air stream at a temperature of 140°–170° C.

4. The composition of claim 1, wherein the product has a bulk density of about 0.3 to 0.6 g/ml.

5. The composition of claim 1, wherein the product has a hygroscopicity such that it absorbs more than 2% water in the course of 24 hours during storage in a hygrostat at a relative humidity of 55%.

6. A compacted article which comprises a composition according to claim 1 and another substance which is a pharmaceutically active compound and/or food substance, compacted together.

7. The compacted article of claim 6, wherein the proportion of the pharmaceutically active compound and/or food substance is from 0.1 to 80%.

8. The compacted article of claim 6, wherein the other substance contains a vitamin and the compacted article is in the form of a vitamin tablet.

9. A chewing gum which comprises a composition according to claim 1 and a gum base.

10. A chewing gum, which comprises:
   15–35% by weight of a gum base,
   40–75% by weight of a composition according to claim 1,
   15–25% by weight of one or more liquid polyhydric alcohol(s), and
   0–5% by weight of one or more aroma substances.

11. A process for the preparation of a composition according to claim 1, which comprises:

a) preparing an aqueous polyol solution consisting essentially of a mixture of 70–98% by weight sorbitol, 1–29% by weight xylitol and 1–9% by weight mannitol based on the total polyol content, b) co-spray-drying the solution into an ascending air stream at a temperature from 120° to 300° C., such that water is evaporated therefrom, and c) isolating the product composition.

* * * * *